US008293294B2

(12) United States Patent
Courtin

(10) Patent No.: US 8,293,294 B2
(45) Date of Patent: Oct. 23, 2012

(54) **COSMETIC COMPOSITION COMPRISING AN AQUEOUS EXTRACT OF *CHRYSOPHYLLUM CAINITO***

(75) Inventor: Olivier Courtin, Neuilly sur Seine (FR)

(73) Assignee: Laboratories Clarins, Cergy Pontoise Cedex (FR)

( * ) Notice: Subject to any disclaimer, the term of this patent is extended or adjusted under 35 U.S.C. 154(b) by 0 days.

(21) Appl. No.: 13/055,278

(22) PCT Filed: Jul. 20, 2009

(86) PCT No.: PCT/FR2009/000890
§ 371 (c)(1),
(2), (4) Date: Feb. 24, 2011

(87) PCT Pub. No.: WO2010/010248
PCT Pub. Date: Jan. 28, 2010

(65) Prior Publication Data
US 2011/0151037 A1 Jun. 23, 2011

(30) Foreign Application Priority Data
Jul. 22, 2008 (FR) ...................................... 08 04170

(51) Int. Cl.
*A61K 36/00* (2006.01)
(52) U.S. Cl. ......... 424/776; 424/777; 424/725; 424/401
(58) Field of Classification Search .................. None
See application file for complete search history.

(56) References Cited

FOREIGN PATENT DOCUMENTS

| JP | 2001-122732 A | 5/2001 |
|---|---|---|
| JP | 2006-265118 A * | 10/2006 |
| WO | 2006/009418 A1 | 1/2006 |

OTHER PUBLICATIONS

Ichimaru Pharcos Inc., JP2001122732, Database WPI, Week 200140, Thomson Scientific, London, GB, XP002518051, May 8, 2001, 2 pages.

M. Ohara et al.: "Cosmetics, bath preparations, and detergents containing moisturizing extracts of *Sapotaceae* plants," Database CA [Online], Chemical Abstracts Service, Columbus, Oh, XP002518050, May 8, 2001, 2 pages.
L. Einbond et al.: "Anthocyanin antioxidants from edible fruits," Food Chemistry, vol. 84, 2004, pp. 23-28.
X. Luo et al.: "Polyphenolic Antioxidants from the Fruits of *Chrysophyllum cainito* L. (Star Apple)," Journal of Agricultural and Food Chemistry, vol. 50, No. 2, 2002, pp. 1379-1382.
C. Choi et al.: "Cosmeceuticals," Seminars in Cutaneous Medicine and Surgery, W.B. Saunders, Philadelphia, US, vol. 25, No. 3, Sep. 1, 2006, pp. 163-168.
"Applications of Oils Extracted from African Star Apple (*Chrysophyllum africanum*), Horse Eye Bean (*Mucuna sloanei*) and African Pear (*Dacryodes edulis*) Seeds," Bioresource Technology, vol. 59, No. 2/03, Jan. 1, 1997, pp. 259-261.
S. Bautista-Banos et al.: "Antifungal activity of leaf and stem extracts from various plant species on the incidence of Collectotrichum gloeosporioides of papya and mango fruit after storage," Database Biosys [Online], Biosciences Information Service, Philadelphia, PA, XP002518203, 2002, 2 pages.
J. Pino et al.: "Volatile constituents of star apple (*Chrysophyllum cainito* L.) from Cuba," Flavour and Fragrance Journal, vol. 17, No. 5, 2002, pp. 401-403.
Terra Services, Water Distribution Specialists, Filtration Systems, printed from http://www.terraservices.ie/other-services/rainwater-harvesting/filtration-systems, 1 page, 2012.
Camarasa et al., "Demonstration of the Anti-Wrinkle Efficacy of a Cosmetic Product. Correlation Between Clinical Observations and Instrument Methods" J. Appl. Cosmetol. 15, 13-20, 1997.
Kueper et al., "Vimentin is the Specific Target in Skin Glycation, Structural Prerequisites, Functional Consequences, and Role in Skin Aging" Journal of Biological Chemistry, vol. 282, No. 32, pp. 23427-23436, 2007.
Rattan et al., "Stress-Mediated Hormetic Modulation of Aging, Wound Healing, and Angiogenesis in Human Cells" N.Y. Acad. Sci. 1119: 112-121, 2007.

* cited by examiner

*Primary Examiner* — Susan Hoffman
(74) *Attorney, Agent, or Firm* — Rothwell, Figg, Ernest & Manbeck, P.C.

(57) ABSTRACT

The invention relates to the field of cosmetics, especially relating to products for controlling skin aging. The invention especially relates to a cosmetic composition including an aqueous fruit extract of *Chrysophyllum cainito*.

9 Claims, 4 Drawing Sheets vimentin (FITC) – nucleus (DAPI)

US 8,293,294 B2

COSMETIC COMPOSITION COMPRISING AN AQUEOUS EXTRACT OF *CHRYSOPHYLLUM CAINITO*

CROSS REFERENCE TO RELATED APPLICATIONS

This application is a 35 U.S.C. §371 National Phase Entry Application from PCT/FR2009/000890, filed Jul. 20, 2009, and designating the United States, which claims priority under 35 U.S.C. §119 to French Patent Application No. 08 04170 filed Jul. 22, 2008, which is incorporated herein in its entirety.

BACKGROUND OF THE INVENTION

1. Field of the Invention

The present invention relates to a cosmetic composition comprising a fruit extract of Chrysophyllum cainito. The present invention also relates to the use of this composition for preventing, for delaying or for combating aging of the skin and/or the appearance of signs of aging of the skin, for example the cutaneous envelope of the breasts. In particular, this composition protects the functionality of the skin cells by inhibiting the glycation of proteins.

2. Description of the Background Art

Glycation is a nonenzymatic process involving a monosaccharide (glucose or ribose), which reacts according to Maillard's reaction with an amine group of an amino acid residue (for example lysine), in particular an amino acid residue of a protein, to form a Schiff base. The latter, after a so-called Amadori molecular rearrangement, can lead, by a succession of reactions, to bridging, in particular intramolecular, for example of the pentosidine type.

This phenomenon is characterized by the appearance of glycation products, the content of which increases regularly as a function of age. The glycation products are for example pyrraline, carboxymethyl-lysine (CML), pentosidine, crossline, $N^{\epsilon}$-(carboxyethyl)-lysine (CEL), glyoxal-lysine dimer, methylglyoxal-lysine dimer, 3DG-ARG imidazolone, versperlysines A, B, C, threosidine or the end products of advanced glycosylation (or AGEs, for Advanced Glycation End Products).

The glycation of proteins is therefore a universal phenomenon, well known with regard to the skin, particularly its dermal component, and principally in relation to collagen fibers. Glycation of collagen in fact increases regularly with age, leading to a regular increase in the content of glycation products in the skin.

The AGEs constitute a heterogeneous group of structures, whereas the carboxymethyl adducts of lysine (CML) occur most widely in vivo. The CMLs with other AGEs accumulate during the intrinsic aging process leading to stiffening and to a loss of elasticity in tissues such as the skin and vessel walls.

It has long been thought that the AGEs result mainly from reaction between proteins and extracellular glucose. However, recent studies indicate that the intracellular formation of AGEs from dicarbonyl compounds resulting from the autoxidation of glucose greatly exceeds the extracellular formation (Shinohara, M et al. (1998) *J. Clin. Investig.* 101, 1142-1147). These dicarbonyl compounds are glyoxal, methylglyoxal, and deoxyglucosone 3, which are substrates for reductases. Glyoxal and methylglyoxal are detoxified by the glyoxalase system. The intracellular AGEs induce an oxidizing stress, activate NF-κB and heme oxygenase, and produce products of lipid peroxidation.

A recent study (Thomas Kueper et al. *J. Biol. Chem.*, Vol. 282, Issue 32, 23427-23436, Aug. 10, 2007) identified vimentin, an intermediate filament protein, as the main target of formation of CMLs (carboxymethyl-lysine), in human skin fibroblasts. The intermediate filaments represent one of the major structural elements of the cytoskeleton in addition to actin microfilaments and microtubules. All the intermediate filament proteins have a secondary structure in common, composed of a central helicoidal domain of about 310 amino acids which is flanked by nonalpha helicoidal domains of variable size. Vimentin is required for numerous essential cellular functions such as cellular motility, chemotactic migration, and cicatrization. Modification of vimentin leads to redistribution of vimentin into a perinuclear aggregate. It is clear that the biological impact of the modification of vimentin is associated with loss of contractile capacity of fibroblasts caused by structural breakdown of the intermediate filament system, finally accelerating the aging process.

Thus, nonenzymatic glycation of proteins shows the primary cause of alteration of skin collagen. One of the important consequences of the glycation of proteins is the creation of free radicals. In fact, when they are affected by glycation, proteins react with oxygen and cause the formation of radicals of the superoxide type. The latter are capable of initiating the degradation of proteins, of altering the membrane structures, and finally disorganizing the extracellular matrix and all its components.

Thus, a cosmetic composition containing active substances capable of halting the glycation of proteins can combat skin aging. The appearance of wrinkles and decrease in skin tonicity reflect the aging of the dermis and notably of its mechanical properties.

In particular, in women, the cutaneous envelope of the breasts is particularly sensitive to aging. In fact, the breasts are a pair of organs overlying the pectoral muscles. The mammary gland is constituted of fat lobules and about twenty glandular lobules located deepest in the gland. The fat lobules give the breast its soft consistency and its shape. The glandular lobules have the task of secretion of the milk conveyed by the lactiferous ducts to the lactiferous sinus opening at the nipple. The excretory ducts are surrounded and supported by a framework of connective tissue. The nipple and areola are a point of fixation of the breast but the skin is the principal means of support of the gland. The skin is connected to the superficial fascia of the gland by the Cooper ligaments. The pectoral muscles do not allow the shape to be altered or the breasts to be remodelled.

With age, hormonal influences, variations in weight but also exposure to sunlight, absence of a brassiere etc., the elastic fibers of the skin may break, and the Cooper ligaments may stretch. The skin loses its tonicity, and the breasts sag: this phenomenon is called ptosis. Mammary ptosis reflects a displacement and sagging of the gland and exaggerated distension of the cutaneous envelope. It is therefore necessary to act on this cutaneous envelope by protecting the proteins from glycation, to prevent aging of the breasts.

SUMMARY OF THE INVENTION

The applicant has demonstrated, surprisingly, that an extract of *Chrysophyllum cainito* inhibits the glycation of proteins. *Chrysophyllum cainito* is a tree of the Sapotaceae family originating from the Greater Antilles. When cut in half, its round fruits reveal a whitish or purple gelatinous pulp around 4 to 10 flattened seeds in a star-shaped cell with 8 or 9 arms. The sweet pulp is more or less liquid, depending on the variety.

Document WO 2006/009418 describes extracts of seeds of Sapotaceae, hydrolyzed enzymatically to give cyanogenic glycosides usable in cosmetics. Document WO 2006/009417 describes a method of obtaining lipids from seeds of Sapotaceae. Document JP 2001 122732 describes cosmetic compositions containing extracts of plants of the Sapotaceae family, said compositions having a hydrating activity capable of preventing problems associated with dry skin such as inflammation and itching. The article by L. Einbond et al., Food Chemistry, 84, 2004, 23-28 describes identification of the presence of antioxidants, in particular of anthocyans, in the fruit of *Chrysophyllum cainito*. The article by Xiao-Dong Luo et al., J. Agric. Food Chem. 2002, 50, 1379-1382, describes identification of the presence of antioxidants, in particular of polyphenols, in the fruit of *Chrysophyllum cainito*. The work by Choi et al., "Cosmeceuticals" Seminars in Cutaneous Medicine and Surgery, W.B. Saunders, Philadelphia, 25 (3), 2006, 163-168, describes the benefit of antioxidants—and more particularly of polyphenols in cosmetic antiaging products. The extract of Chrysophyllum cainito of the present invention differs from the extracts of the prior art in that it is an aqueous extract of the whole fruit, i.e. of the seed, the pulp and the pericarp of the fruit, the chemical composition of which is different from the extracts of the prior art. Moreover, no document discloses or suggests an effect of an extract of *Chrysophyllum cainito* on the glycation of proteins, and in particular on ptosis of the breasts.

The cosmetic composition of the present invention contains an aqueous fruit extract of *Chrysophyllum cainito*. Advantageously, this extract comprises an extract of the pericarp and of the pulp of the fruit of *Chrysophyllum cainito*. Preferably it is a dry extract obtained by a method comprising at least the following stages:
  grinding of the dry fruits in a bowl
  addition of water (room temperature) to cover the fruits
  maceration for at least 24 h
  primary filtration This dry extract is advantageously obtained according to the following protocol:
  (i) Aqueous extraction of the fruits of *Chrysophyllum cainito*:
  grinding of the dry fruits in a bowl
  addition of water (room temperature) to cover the fruits
  slow stirring
  maceration for at least 24 h
  primary filtration
  (ii) Concentration:
  measurement of the dry matter content
  passage through the concentrator (low temperature, low pressure)
  (iii) Addition of maltodextrin and sterilization
  (iiii) Drying and debacterialization:
  atomization of the concentrate in the spraying tower
  sieving of the powder obtained and packaging
  treatment by ionization for debacterialization.

The dry extract of *Chrysophyllum cainito* used in the composition according to the invention is a beige powder with a characteristic odor. It has the following analytical characteristics:
  solubility=10% in water.
  water content<10%.
  pH=5-7.
  granulometry 500 microns.
  total sugars=20-50%/dry matter.
  polyphenols (expressed as catechin)-0.1-1%/dry matter.

Preferably the cosmetic composition according to the invention comprises from 0.1 to 10% of extract of *Chrysophyllum cainito* by weight of dry matter relative to the total weight of the composition. Advantageously, the composition comprises from 0.1 to 5 wt. % of extract of *Chrysophyllum cainito* by weight of dry matter relative to the total weight of the composition.

The compositions according to the invention can further comprise one or more formulation agents or additives with known, conventional use in cosmetic and dermatological compositions such as, as nonlimiting examples, emollients, colorants, film-forming agents, surfactants, perfumes, preservatives, emulsifiers, oils, glycols, vitamins such as vitamin E, UV filters, etc. Based on his knowledge in the area of cosmetics, a person skilled in the art will know which formulation agents to add to the compositions of the invention and in what amounts depending on the required properties.

The compositions according to the invention can be in any form known by a person skilled in the art in the field of cosmetology and dermatology without other galenic restriction than application on the face and on the body. Advantageously, the compositions according to the invention are in the form of a gel, a cream, a lotion, an oil, a milk, a spray, etc.

The cosmetic composition according to the invention can be used for preventing, for delaying or for combating aging of the skin and/or the appearance of signs of aging of the skin. "Signs of aging of the skin" means: wrinkles, lines, sagging of the skin, loss of elasticity of skin fibers, withered skin, thin skin, and skin that is dull and/or without radiance.

The cosmetic composition according to the invention can be used as a protein antiglycation agent.

The cosmetic composition according to the invention can be used for preventing and/or delaying and/or correcting ptosis of the breasts.

The invention further relates to a method of cosmetic treatment comprising the application of a composition as described above, which comprises at least one aqueous extract of *Chrysophyllum cainito* and a cosmetic vehicle, on the skin. This method is intended to prevent, delay or combat aging of the skin and/or the appearance of signs of aging of the skin, to prevent and/or delay and/or correct ptosis of the breasts, and to prevent or treat glycation of proteins of the skin.

It is recommended to apply it one or more times a day (from one to five times a day as a general rule), for a duration from several days to several months. Application can be localized on the zones of the body that are more particularly subject to the effects of aging, such as the face and the breasts, the abdomen, but application can be on the whole body. Application is preferably accompanied by massaging of the skin.

The following examples relate on the one hand to evaluation of inhibition of the glycation of proteins by an extract of *Chrysophyllum cainito*, and on the other hand compositions according to the present invention.

BRIEF DESCRIPTION OF THE DRAWINGS

The examples refer to the following figures, in which.

DETAILED DESCRIPTION OF A PREFERRED EMBODIMENT

I. Evaluation of the Inhibition of Protein Glycation by an Extract of Chrysophyllum Cainito

A. Material and Method

1) Method

It is a question of evaluating the inhibitory activity of the extract of *Chrysophyllum cainito* with respect to CML (carboxymethyl adducts of lysine) induced by glyoxal as well as its protective effect on vimentin, the target of formation of the CMLs, in a culture of human dermal fibroblasts.

Normal adult human fibroblasts were cultivated at 37° C. and 5% CO2 on a cover slip in a Petri dish of diameter 60 at a rate of 30000 cells per cover slip. The incubation medium is DMEM medium (Dulbecco modified Eagle medium) supplemented with 10% fetal calf serum and penicillin/streptomycin (50 µg/ml). The fibroblasts were incubated for 7 days in the medium described above supplemented with 200 µM of glyoxal (derived from glucose). The culture set up in this way constitutes a relevant model of glycation in vitro.

2) Material

The products tested are as follows:
control (without glyoxal)
untreated control
Aminoguanidine 10 mM (positive reference)
*Chrysophyllum cainito* at 0.1%
*Chrysophyllum cainito* at 0.25%
*Chrysophyllum cainito* at 0.5%

To reveal a glycation inhibiting effect, the *Chrysophyllum cainito* extract is added at the same time as the glyoxal. To validate the experiment, aminoguanidine, a known inhibitor, is used as a positive reference. A control of medium alone without glyoxal is added.

At the end of incubation (D7), each cellular lawn is rinsed, fixed with methanol at −20° C. before proceeding to detection of vimentin or of CML by immunofluorescence.

3) Immunolabeling

The cells were washed with PBS (phosphate-buffered saline) and permeabilized with 0.1% Triton X-100 for 10 minutes. The nonspecific sites are saturated with a solution of bovine serum albumin 2% (PBS-BSA 2%) for 10 minutes at room temperature. The cells were then incubated with the primary antibody in 1% BSA for 1 h (primary antibodies detecting vimentin (dilution 1:100) or CML (dilution 1:50)). After incubation, the cells were washed with PBS and then incubated for 1 h with a solution of 1% BSA containing specific secondary antibody bound to a fluorochrome FITC (fluorescein-5-isothiocyanate) or TRITC (tetramethyl rhodamine isothiocyanate) and directed against the primary antibody. Before taking the reading, 4 rinsings with PBS are performed.

Figure 1:
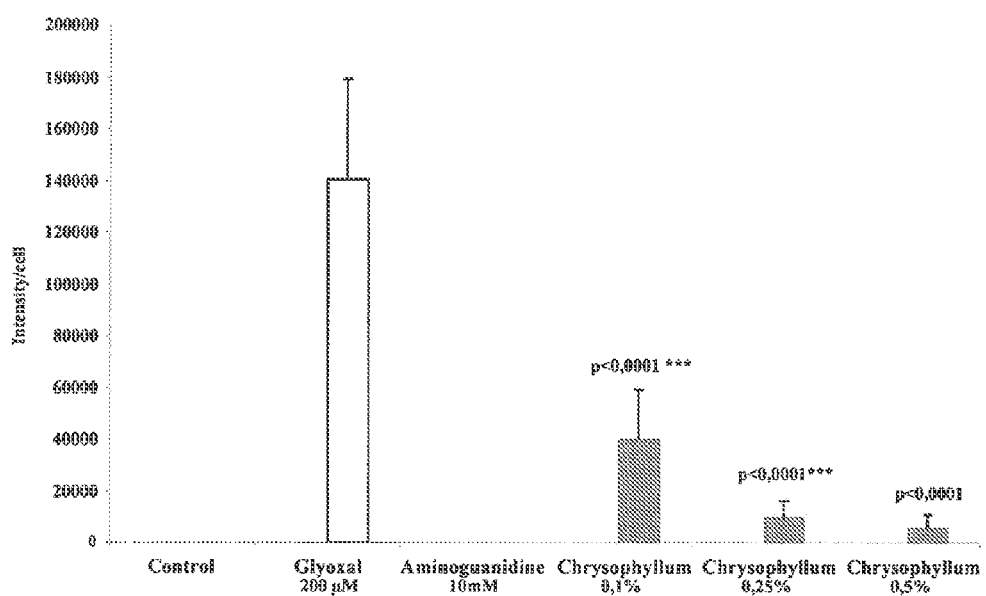
FIG. 1 shows measurement of the intensity of fluorescence as a function of the active substance present in the culture medium: glyoxal alone or glyoxal with a glycation inhibitor.
Figure 2:
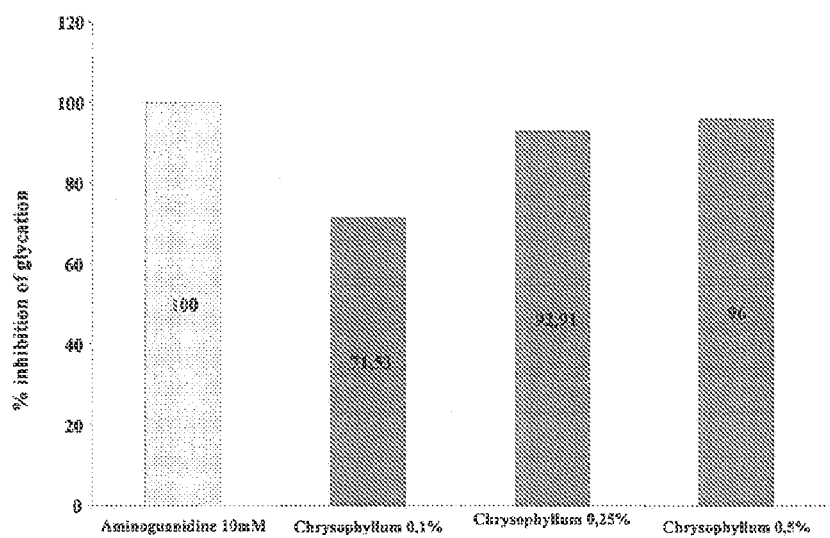
FIG. 2 shows the percentage inhibition of glycation relative to the untreated control as a function of the active substance present in the culture medium: glyoxal with a glycation inhibitor.
Figure 3:
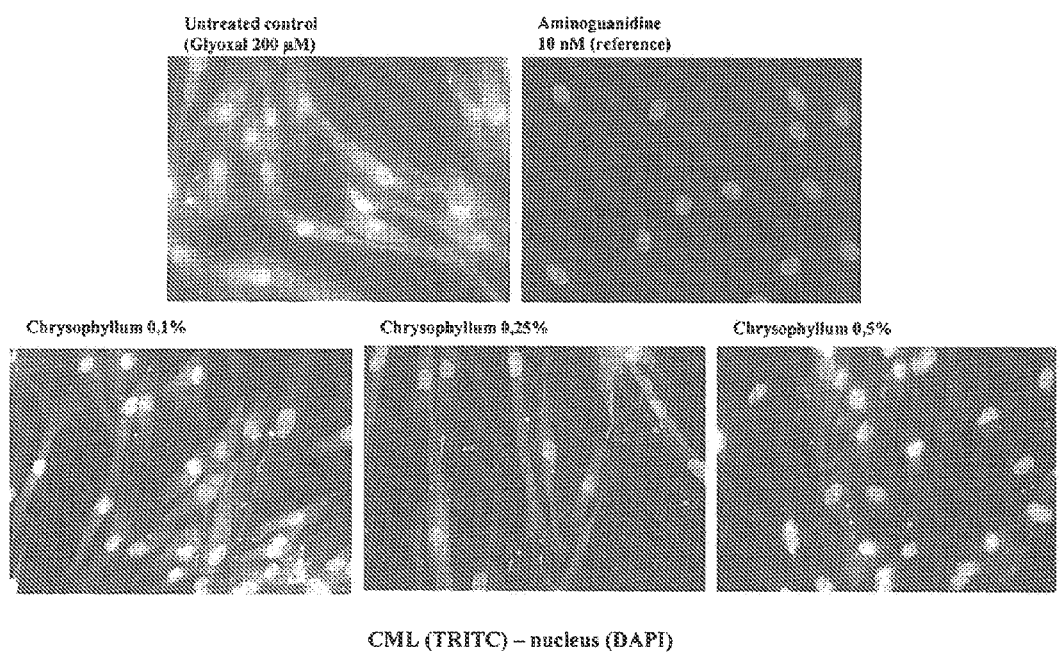
FIG. 3 shows fluorescence micrographs of fibroblasts at 200× magnification.
Figure 4:
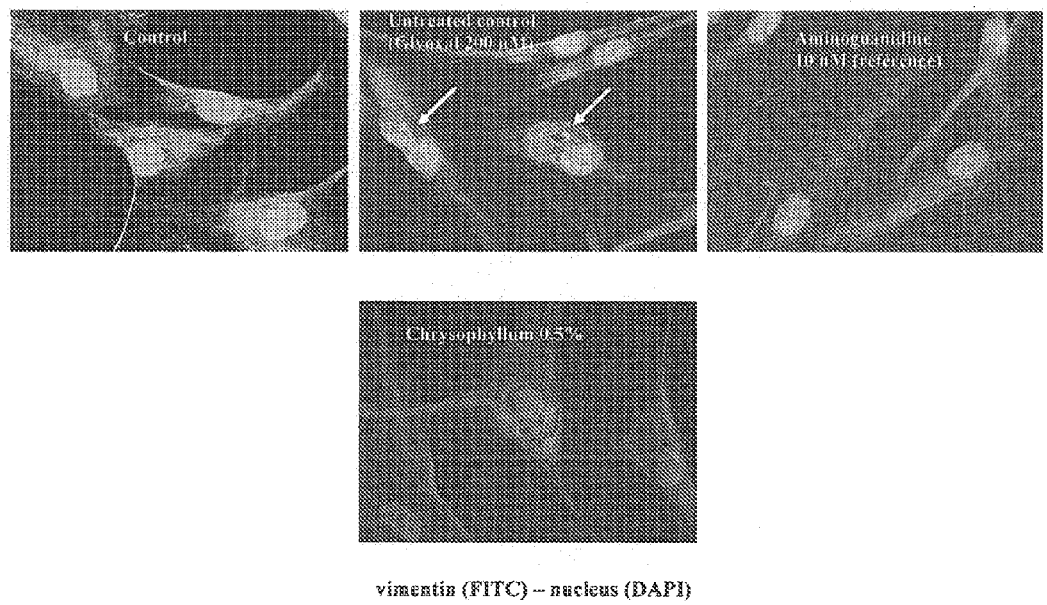
FIG. 4 shows an enlargement of the micrographs in FIG. 3 at 400× magnification.

The cover slips are mounted on the glass slide and then examined with the fluorescence microscope (Nikon Eclipse 50i). Several fields of the cellular population are photographed. The photomicrographs are analyzed using Lucia image analysis software. The FITC fluorescence images indicate the regions of localization of vimentin. The TRITC fluorescence images indicate the regions of localization of CML. The DAPI fluorescence images indicate the cell nuclei and therefore the number of cells per field (see FIGS. 1 to 4).

B. RESULTS

1) Formation of CMLs

The intensity of labeling of CML was observed on photomicrographs for the conditions 'untreated control' and extracts of *Chrysophyllum cainito* at 3 concentrations.

This intensity of fluorescence is shown relative to the number of cells per micrograph.

For the condition 'treatment with aminoguanidine', positive reference, just 4 micrographs were sufficient to validate the experiment. The aminoguanidine, having completely inhibited the generation of CMLs, causes absence of any intensity of labeling.

Analysis of variance (Anova) is used for investigating the differences in mean value between populations. This method uses measurements of variance in order to determine whether or not the differences in mean value measured on the populations are significant.

Aminoguanidine, positive reference, completely inhibits the formation of carboxymethyl adducts of lysine and validates our experiment.

In these experimental conditions, the *Chrysophyllum cainito* extract shows dose-dependent inhibition of the formation of CMLs. For an optimal dose of 0.5% used in vitro, the *Chrysophyllum cainito* extract almost completely inhibits the formation of adducts that cause glycation.

2) Formation of CMLs

In these experimental conditions, treatment of human dermal fibroblasts with glyoxal modifies vimentin, leading to redistribution of the intermediate filament into perinuclear aggregate (see arrows).

The *Chrysophyllum cainito* extract used at a concentration 0.5% inhibits the effect of glyoxal on vimentin.

C. Conclusion

The *Chrysophyllum cainito* extract has a vimentin protecting effect with respect to dicarbonyl compounds such as glyoxal, which induces structural modifications of this intermediate filament by forming carboxymethyl adducts of lysine or CML.

Inhibition of the glycation of vimentin delays the cellular aging process and enables dermal fibroblasts in vitro to preserve their motility and their contractile capacity, which are important in the cicatrization process.

II. Examples of Formulation

The percentages are percentages by weight relative to the total weight of the composition.

W/O Emulsion

|  | % |
|---|---|
| PEG 30 DIPOLYHYDROXYSTEARATE | 4.00 |
| HYDROGENATED C16-C18 TRIGLYCERIDES | 5.00 |
| PEG-45/DODECYL GLYCOL COPOLYMER | 1.20 |
| $C_8C_{10}$ TRYGLYCERIDE | 19.00 |
| LIQUID PARAFFIN | 8.00 |
| GLYCOLS | 10.00 |

|  | % |
|---|---|
| EXTRACT OF *CHRYSOPHYLLUM* | 2.50 |
| OAT POLYSACCHARIDES | 1.00 |
| DEMINERALIZED WATER | Q.S. 100 |

Lotion

|  | % |
|---|---|
| GLYCOL | 2.00 |
| SODIUM CHLORIDE | 1.00 |
| ETHANOL | 5.00 |
| EXTRACT OF *CHRYSOPHYLLUM* | 0.50 |
| TROMETHAMINE | 0.80 |
| PRESERVATIVES | 0.50 |
| SOLUBILIZER | 0.30 |
| PERFUME | 0.10 |
| DEMINERALIZED WATER | Q.S. 100 |

Gel

|  | % |
|---|---|
| CARBOXYMETHYLCELLULOSE | 0.03 |
| CARBOMER | 0.60 |
| SODA | 0.17 |
| GLYCEROL | 5.00 |
| EXTRACT OF *CHRYSOPHYLLUM* | 0.50 |
| D-PANTHENOL 75L | 0.30 |
| OAT POLYSACCHARIDES | 1.00 |
| VITAMIN A PALMITATE | 0.10 |
| TOCOPHEROL ACETATE | 0.05 |
| HYDROGENATED CASTOR OIL PEG-40 | 1.35 |
| CHELATING AGENT | 0.03 |
| PRESERVATIVES | 0.50 |
| COLORANT | 0.017 |
| PERFUME | 0.30 |
| DEMINERALIZED WATER | Q.S. 100 |

O/W Emulsion

|  | % |
|---|---|
| ACRYLOYL DIMETHYL TAURATE/VP COPOLYMER | 0.70 |
| HELIOGEL ® | 0.50 |
| GLYCOLS | 5.00 |
| CARBOMER | 0.50 |
| SODA | 0.055 |
| CARBOXYMETHYLCELLULOSE | 0.30 |
| $C_8C_{10}$ TRYGLYCERIDE | 4.50 |
| DICAPRYLYL CARBONATE | 6.00 |
| SYNTHETIC ESTER | 3.00 |
| SILICONE OIL | 1.50 |
| TOCOPHEROL ACETATE | 0.05 |
| VITAMIN A PALMITATE | 0.10 |
| D-PANTHENOL 75L | 0.20 |
| EXTRACT OF *CHRYSOPHYLLUM* | 0.50 |
| PRESERVATIVES | 0.10 |
| CHELATING AGENT | 0.20 |
| PERFUME | 0.30 |
| DEMINERALIZED WATER | Q.S. 100 |

The invention claimed is:

1. A method for inhibiting the glycation of proteins by applying to the skin an effective amount of a cosmetic composition comprising an aqueous extract of *Chrysophyllum cainito* consisting of an extract of the seed, the pericarp, and the pulp of the fruit of *Chrysophyllum cainito*.

2. The method according to claim 1, wherein said aqueous extract is obtained by a method comprising at least the following stages:
grinding dry fruit seed, pericarp, and pulp in a bowl;
adding water at room temperature to cover the fruit seed, pericarp, and pulp;
macerating for at least 24 h: and
performing primary filtration.

3. The method according to claim 1, wherein the composition comprises 0.1 to 10% of said aqueous extract by weight of dry matter relative to the total weight of the composition.

4. The method according to claim 1, wherein the composition further comprises at least one formulation agent or additive selected from emollients, colorants, film-forming agents, surfactants, perfumes, preservatives, emulsifiers, oils, glycols, UV filters, and vitamins.

5. The method according to claim 1, wherein the composition is in a form of a gel, a cream, a lotion, an oil, a milk or a spray.

6. The method according to claim 1, wherein the composition is applied for at least one of, delaying aging of skin, combating aging of skin, delaying appearance of signs of aging of skin, or combating appearance of signs of aging of skin.

7. The method according to claim 6, characterized in that the signs of aging of the skin are selected from at least one of wrinkles, lines, sagging of the skin, loss of elasticity of skin fibers, withered skin, thin skin, skin that is dull, or skin that is without radiance.

8. The method according to claim 1, wherein the composition is applied for at least one, delaying ptosis of breasts or correcting ptosis of breasts.

9. The method according to claim 3, wherein the composition comprises from 0.1 to 5 wt. % of said aqueous extract by weight of dry matter relative to the total weight of the composition.

* * * * *